United States Patent [19]

O'Keefe

[11] 3,995,371

[45] Dec. 7, 1976

[54] ELECTROLESS PLATING METHOD FOR TREATING TEETH

[75] Inventor: Thomas J. O'Keefe, Rolla, Mo.

[73] Assignee: The Curators of the University of Missouri, Columbia, Mo.

[22] Filed: Oct. 10, 1974

[21] Appl. No.: 513,654

[52] U.S. Cl. .................................. 32/15; 204/38 B; 427/2; 427/4; 427/304; 427/305; 428/16
[51] Int. Cl.² ...................... A61K 5/02; C23C 3/02
[58] Field of Search ............ 32/15; 428/16, 13, 15; 427/304, 305, 306, 4, 2; 204/38 B, 20; 63/2, 21, 23; 156/57

[56] References Cited

UNITED STATES PATENTS

| | | | |
|---|---|---|---|
| 2,454,610 | 11/1948 | Narcus | 427/304 |
| 2,464,143 | 3/1949 | Martinson | 427/304 |
| 2,702,253 | 2/1955 | Bergström | 427/304 |
| 2,802,268 | 8/1957 | Knappwost | 32/15 |
| 3,093,509 | 6/1963 | Wein | 427/306 |

FOREIGN PATENTS OR APPLICATIONS 284,786   2/1928   United Kingdom ............... 427/304

*Primary Examiner*—Ralph S. Kendall
*Attorney, Agent, or Firm*—Koenig, Senniger, Powers and Leavitt

[57] ABSTRACT

An electroless plating method for providing a thin adherent substantially continuous metallic layer over an osseous substrate such as a tooth structure. The method comprises contacting the substrate with an aqueous plating mixture containing a water-soluble salt of a metal selected from the group consisting of gold, silver, copper, nickel, platinum, palladium and tin, and a reducing agent for the metal ions of said salt. The plating mixture is maintained in contact with the substrate for a time sufficient for the metallic layer to form thereon. The metallic layer so provided is adapted for subsequent application of a tooth restorative material such as a dental amalgam for carrying out a tooth restoration.

28 Claims, No Drawings

ELECTROLESS PLATING METHOD FOR TREATING TEETH

BACKGROUND OF THE INVENTION

This invention relates to the field of dentistry and more particularly to a method for providing a thin adherent substantially continuous metallic layer over an osseous substrate. In particular, this invention relates to a method for providing a metallic layer over a tooth surface which may serve as a substrate for the subsequent application of an amalgam or other metal filling.

In the practice of dentistry, the restoration of a locally decayed tooth is commonly accomplished by excavating the tooth to remove the decayed portion and filling the excavation with an amalgam. Although this procedure is satisfactory in many respects, its effectiveness for preserving the tooth is limited due to the low level of adherence which exists between the amalgam and the tooth structure at the surface of the excavation. Except for weak van der Waals forces, there is essentially no chemical adhesion between amalgam and an osseous substrate such as tooth structure.

As a consequence of the poor adhesion between amalgam and the tooth, it is generally necessary to drill an excavation in the tooth larger than that required simply to remove the portion of the tooth affected with caries. Undercut recesses are provided within the excavation for mechanical attachment of the amalgam filling to the tooth. The filling is then keyed into these undercut portions so that tooth and filling are mechanically locked together. This procedure adversely affects long term preservation of the tooth because of the relatively large portion of the tooth which must be removed as compared to the size of the portion affected by caries. Moreover, the restoration itself not only fails to positively prevent further decay of the tooth but may actually promote such decay due to secondary caries arising from the percolation of oral fluids through a narrow gap which may exist between the filling and the surface of the excavation. Such a gap may exist because of the lack of adherence between the filling amalgam and the tooth structure, and the resultant percolation of oral fluids may cause secondary caries at the surface of the excavation under the filling.

A need has existed in the art, therefore, for an improved dental restorative technique which provides strong adherence between an amalgam or other type of filling and a tooth excavation so that a filling may be securely applied without the necessity of the relatively large excavations required for mechanical attachment of the filling to the tooth. A need has further existed for such a technique which may eliminate gaps between the surface of the filling and the surface of the excavation through which oral fluids may percolate. In the literature, suggestions have been made to accomplish these results by electroplating. See, for example, Franklin, "Electrodeposition in Dentistry", Plating, Vol. 58, No. 8, August, 1971. However, such general suggestions have apparently not been reduced to a practical method useful in the restoration of teeth.

SUMMARY OF THE INVENTION

It is an object of the present invention, therefore, to provide an improvement in dental restorative techniques whereby the adhesion of an amalgam filling to a tooth excavation may be significantly improved. It is a particular object of the invention to provide a method for applying over a tooth structure an intermediate layer which is strongly adherent both to the tooth structure and to a dental amalgam or other filling material which may subsequently be applied. It is a general object of the present invention to provide a method for applying over an osseous substrate, such as tooth or bone, a thin layer of metal which may seal the substrate against contact with or penetration by materials such as oral fluids. Other objects and features will be in part apparent and in part pointed out hereinafter.

In its essential aspect, therefore, the present invention is directed to an electroless plating method for providing a thin adherent substantially continuous metallic layer over an osseous substrate. The method comprises contacting the substrate with an aqueous plating mixture containing a water-soluble salt of a metal selected from the group consisting of gold, silver, copper, nickel, platinum, palladium and tin and a reducing agent for the metal ions of the salt. This mixture is maintained in contact with the substrate for a time sufficient for the metallic layer to form thereon. The invention is further directed to such a method in which the metallic layer is contacted with an aqueous solution containing ions of a second metal having a lower oxidation potential than the metal of the layer. Contact with the solution containing ions of the second metal causes oxidation of the metal of higher oxidation potential and displacement thereof from the surface of the layer with concomitant reduction of the ions of the second metal to the elemental state and deposition of the second metal on the surface. Also included in the invention is a method whereby the thin adherent substantially continuous metallic layer is applied to the surface of an excavation made in the course of a tooth restoration, and a tooth restorative material such as an amalgam is applied over the layer.

DESCRIPTION OF THE PREFERRED EMBODIMENTS

It has now been discovered that electroless plating techniques may be utilized to provide a thin continuous coating of silver, copper, nickel, gold, platinum, palladium or tin on the surface of an osseous substrate such as tooth or bone. Continuity of the metal layer is indicated by the relatively high conductivity thereof. Thus, resistivities as low as 1–10 ohms/cm have been measured across a metal coating applied to the surface of the tooth in accordance with the invention. The metal layer is also highly adherent to the osseous substrate and resists removal upon application of tensile forces as high as 500–1,000 psi normal to the surface. The thickness of the metal layer is typically 1–10μ.

Because of its continuity, as indicated by its low resistivity, the metal layer applied in accordance with the method of the invention continuously covers and substantially seals the area of the substrate to which it has been applied. Thus, the metal layer constitutes a protective film which prevents penetration of oral fluids into pits and fissures in the tooth enamel so that tooth decay may be inhibited. Also, any other material such as a dental amalgam which tends to alloy with or otherwise strongly adhere to the metal layer may be applied thereover and in effect become strongly adhered to the osseous substrate and sealed over that substrate. In case of a tooth restoration, such strong adherence and sealing may effectively prevent percolation of oral fluids which may otherwise tend to promote the initiation of secondary caries.

The substrate for the method of the invention may be an osseous substrate such as tooth or bone. Although the invention is primarily concerned with the application of an adherent metal layer to a surface of a tooth, it is also applicable to the provision of a metal layer on the surface of bone and may thus be useful in surgical procedures as an intermediate step which facilitates grafting a synthetic bone or other prosthetic device to a human bone.

In accordance with the process of the invention, the osseous substrate may optionally be mechanically abraded or chemically etched before it is contacted with the electroless plating mixture. Etching with a solution of phosphoric acid, acetic acid, or hydrochloric acid may be essential in some instances to remove foreign substances and generally results in the subsequent application of a more uniform metal layer, which frequently has a honeycomb type of appearance. Other acids such as sulfuric, nitric and hydrofluoric are also effective but are not suitable for use in dental treatment procedures. Phosphoric acid solutions having an acid strength of 50–80% by weight are especially preferred for etching. After etching, residual etchant acid is preferably neutralized by application of an alkali or other base before proceeding with the plating operation.

Abrasion of the substrate may also be useful, particularly in the removal of plaque and dried blood from areas to be plated. Where the substrate is both abraded and etched, abrasion is normally carried out first.

In applying the metal layer, a discontinuous layer of an activating metal may be initially deposited on the substrate using conventional sensitizers and activators, such as stannous chloride and palladium chloride, respectively. Advantageously, stannous fluoride is used in place of stannous chloride because of the recognized decay-prophylactic effect of stannous fluoride. Sequential treatment with solutions containing stannous ions and palladium ions produces evenly distributed palladium nuclei on the surface of the substrate, nuclei which catalyze the plating step itself in which a continuous layer of silver, copper, nickel, gold, platinum, palladium or tin is applied. Normally, the surface is first activated with a palladium solution and then sensitized with a stannous solution but the reverse order may also be followed. Conveniently, a sensitizing solution may contain on the order of 15 g/l stannous ions and 15 ml/l of hydrochloric acid, while an activating solution may be approximately 0.09 molar in palladium ion and 0.18 molar in hydrochloric acid.

In the method of the invention, it has been found that $Sn^{++}/Pd^{++}$ sensitization and activation is not essential and is preferably dispensed with where a silver layer is applied from an aqueous plating mixture comprising a silver salt and a reducing agent. Even in the absence of palladium nuclei on the tooth surface, silver ions react with the reducing agent on initial contact with the substrate to form a discontinuous, non-conductive deposit of silver thereon, which then activates the substrate for further deposit of silver to provide a continuous conductive silver layer. Any metal which deposits to some extent on a previously metal-free surface is considered self-activating and a continuous layer may be obtained by repeated application of the metal solution and a reducing agent, without initial palladium activation.

The aqueous plating mixture may be applied to the substrate in any convenient manner, for example, by immersion. Swabbing, however, has also been found to be effective and is preferred in the case of in vivo tooth treatment since it avoids the oral dams and attendant procedures required for immersion. The salt of the metal to be plated is preferably applied to the surface of the substrate in an aqueous salt solution, although a slurry may also be utilized. Where a salt solution is employed, it should be at least 0.25 molar in the ions of the metal to be plated, and preferably should contain on the order of 100 gpl of said ions. The reducing agent may be incorporated in this salt solution, or may be applied in sequence with the salt solution, to provide the aqueous mixture with which the substrate is contacted to effect the plating reaction. Where a copper salt solution containing a reducing agent is used, it has been observed that adherent conductive metal layers are more consistently obtained if the solution is aged for at least several hours, for example, overnight, before use in electroless plating of an osseous substrate such as a tooth.

In order to effect rapid and uniform distribution of the aqueous plating mixture over the substrate to be plated, a conventional wetting agent may be incorporated in this mixture. Such a wetting agent may be included in the aqueous plating mixture as it is applied to the substrate or, alternatively, the substrate may be contacted with the wetting agent prior to contact with the aqueous plating mixture. In either event, the wetting agent is present in the plating mixture.

Although essentially any water-soluble salt of silver, copper, nickel, gold, platinum, palladium and tin may be used for plating, it is preferred that chloride ions be excluded from the plating mixture if any subsequent operation is to involve the plating of silver. Because of the insolubility of silver chloride, the presence of residual chloride ions remaining from earlier applications tends to interfere with the effectiveness of silver plating. The use of chloride salts is suitable, however, where a silver layer is laid down prior to the plating of another metal from its chloride salt. Among the particular salts which are useful in the method of the invention are silver nitrate, silver fluoride, copper sulfate, palladium chloride, nickel chloride, gold chloride and platinum chloride.

Because of the potential for metal precipitation from solutions of the salts of more noble metals, a complexing agent may optionally be included in the salt solution applied to the substrate. Ammonium hydroxide is a useful complexing agent, particularly in the case of silver salts. Other conventional stabilizers and complexing agents, such as Rochelle salt and ethylenediaminetetraacetic acid, may also be utilized.

Reducing agents which may be used in the method of the invention include formaldehyde, hydrazine, dimethylaminoborane, alkali metal formates and alkali metal hypophosphites. Formaldehyde and hydrazine are particularly useful reducing agents. Where formaldehyde is used, the pH should be controlled above about 8.5 to insure maximum effectiveness. If ammonium hydroxide is utilized for controlling pH in the plating of silver with formaldehyde, the pH should be maintained in the range of between about 8.5 and about 10. At pH's above 10, the amount of ammonia present is sufficient to complex the silver so strongly that the progress of the plating reaction is adversely affected. If the tooth is acid etched prior to electroless plating and formaldehyde is used for reduction, an alkaline wash is preferably made before application of the plating mixture.

Where the reducing agent is hydrazine, the amount incorporated in the aqueous plating mixture should be limited to avoid bulk precipitation of the metal in particles which are not adherent to the substrate. A concentration on the order of 0.5–5.0 ml hydrazine/l plating mixture is preferred.

Stannous salts and ferrous salts are also used to advantage as reducing agents in the method of the invention. Stannous salts, of course, act as reducing agents in the activation/sensitization step where activation/sensitization is carried out by deposit of palladium nuclei on the tooth. It will be recognized that the distinction between the activation/sensitization and reduction steps is in part semantical, activation/sensitization connoting the reductive deposit of nuclei of a catalyzing metal such as palladium while reduction (plating) connotes application of a continuous layer of the metal comprising the bulk of the plating layer. Where no activation/sensitization step as such is carried out, the initial nuclei are deposited from the plating mixture itself. In all instances, the continuous metal layer is obtained from repeated application of the plating mixture, or by cementation, as described below. Where stannous salts are used for reduction, a minor proportion of $Sn^{+4}$ ions are preferably present to enhance wettability. However, a ferrous salt solution used for reduction should be substantially free of ferric ions.

Once a base metallic layer has been plated over the osseous substrate, a layer of another more noble metal can be applied over the first layer by cementation. This technique can be carried out even if the base layer is not continuous. In a cementation process, the first metal layer is contacted with an aqueous cementation solution containing ions of the second more noble metal. Since the second metal has a lower oxidation potential than the metal of the first layer, the first metal is oxidized and displaced from the surface of the layer, and ions of the cementation solution are concomitantly reduced to the elemental state and the second, more noble, metal is deposited on the surface of the first layer. Cementation is effective for plating silver over copper, and is also effective for the plating of gold, platinum or palladium over silver, copper or tin. In an especially advantageous embodiment of the invention, the substrate is first activated by deposit of an activating metal, for example, silver, from a plating mixture containing a silver salt and a reducing agent, the activated substrate is contacted with an aqueous plating solution to provide a layer of a first plating metal, for example, copper, and another layer of a more noble metal (such as silver) is provided by cementation on the first layer. Alternate layers of the two metals may then by repetitively laid down to build up the thickness of metal on the substrate.

In one particularly preferred embodiment of the invention, the substrate is etched with acetic or phosphoric acid and then contacted with a plating solution containing a silver salt and a reducing agent to provide a silver deposit which activates the substrate for the reception of further metal deposits. A plating mixture comprising a copper salt and a reducing agent is then applied to provide a copper layer over the substrate. Thereafter, the substrate is alternately contacted with a silver solution from which a silver deposit is obtained by oxidative displacement of copper and with an aqueous mixture containing a copper salt and a reducing agent to provide a further layer of copper. The metallic layer is built up to the desired thickness and continuity by repeating the alternate application of silver and copper reducing agent solutions as many times as necessary. Typically four to eight repetitions of this procedure provide highly satisfactory results. In another highly preferred procedure, a layer consisting entirely of silver is built up by repeated application of a solution containing silver salt and a reducing agent.

The method of the invention operates at room temperature to rapidly provide a continuous conductive metal coating on an osseous substrate. Although higher temperatures (e.g., up to 45° C. without anesthesis) can be tolerated, even in an in vivo dental procedure, plating at room temperature is sufficiently rapid to provide a conductive metallic layer having a resistance as low as 1– ohms in a period of 2 ½– 5 min.

In a further embodiment of the invention, after a metal layer has been deposited on the substrate by electroless plating, the thickness of the layer may be increased by electrolytic plating wherein the initial metal deposit is the cathode. Conveniently, a brush plating apparatus is used for this purpose. Such an apparatus includes a direct current power source and a stylus having an insulating handle and a carbon tip which is electrically connected to the positive terminal of the power source and serves as an anode. The negative terminal of the power source is electrically connected to the metal layer. An absorbent material such as a cotton ball attached to the carbon tip holds an electrolytic solution which is highly concentrated with respect to ions of the metal to be electroplated. To effect plating, the cotton ball on the end of the stylus is pressed against the surface to be plated so that the plating solution is in contact with both the metal layer cathode and the carbon tip anode, and a direct plating current is applied at a voltage of about 2.5 v. The plating current is typically 10–100 ma.

The electrolessly deposited initial layer may be electroplated with essentially any desired metal. A silver deposit, for example, may be electroplated with tin, copper, gold, nickel, palladium, chromium, etc. One particularly useful brush plating system is the Dalic Process sold by Sifco Metachemical of Clevelang, Ohio.

The method of the invention is especially suitable as a step in a tooth restoration operation preliminary to the insertion of a gold foil or dental amalgam filling. The metallic layer obtained by the method of the invention not only effectively seats the pits and fissures at the surface of the tooth structure, but is strongly adherent both to the tooth and to an amalgam subsequently applied. Thus, the dentist may avoid the deep excavations, extending beyond the caries-affected portion of the tooth, which are otherwise necessary to provide the undercut portions to which the amalgam is mechanically attached. In the process of inserting amalgam over the electrolessly plated metallic layer, it is preferable to rub a small fraction of the amalgam into the metallic layer before the bulk of the filling is inserted thereover. In this way, the thickness of metal on the tooth structure is further built up before the mass of amalgam is applied and the risk of washing off the metallic layer by dissolution in the amalgam is thereby avoided.

Where a deep excavation must be made to remove the caries-affected portion of a tooth, the predentin may be exposed, in which case the method of the invention cannot be used to coat the entire excavation with metal. While this method affords a continuous adherent coating of metal over tooth enamel or other osseous tooth material, it is not effective for coating of the predentin, which is organic matter. Nonetheless, the method of the invention remains highly useful in such circumstances since it may be carried out to provide a coating about the edges or rim of the excavation. The predentin is treated with a resin such as copal-based dental varnish and the filling subsequently installed. By bonding the filling to the metal coating at the rim of the excavation, a tight seal is provided which prevents percolation of oral fluids between the filling and the excavation surface. Formation of secondary caries is thereby inhibited.

As noted, the metal layer deposited in accordance with the method of the invention is useful for sealing of pits and fissures in a tooth regardless of whether the tooth is excavated before metal deposition and filled thereafter. Even when used to seal pits and fissures in a nonexcavated tooth, however, the electrolessly deposited metal layer preferably serves as a substrate for a thicker layer of another metal of demonstrated resistance to oral fluids, such as dental amalgam, which adheres to the electroless deposit.

Those skilled in the art will recognize that the capability of providing a continuous metal substrate allows the dentist the option of considering materials other than conventional dental amalgam and gold foil as the substance of a tooth restoration. Thus, any metal which alloys with or otherwise adheres to the metal substrate at the temperatures and pressure attainable in restorative procedures is a potential candidate for use as the restorative material.

The following examples illustrate the invention.

EXAMPLE 1

The following solutions were prepared for use in electroless plating (Percentages are by weight except where stated otherwise):

| Copper Salt Solution A$_1$ | | |
|---|---|---|
| Rochelle Salt | 170 | g/l |
| NaOH | 50 | g/l |
| CuSO$_4$ . 5H$_2$O | 35 | g/l |
| Na$_2$CO$_3$ | 30 | g/l |
| Disodium ethylenediaminetetraacetic acid sold under the trade designation "Versene T" by the Dow Chemical Company | 60 | parts/million |
| Water | balance | |
| Copper Salt Solution A$_2$ | | |
| CuSO$_4$ . 5H$_2$O | 4.8 | g |
| Formaldehyde (37% aqueous solution) | 5.4 | ml |
| H$_2$O | 120 | ml |
| Silver Salt Solution B$_1$ | | |
| Part A AgNO$_3$ in water | 50 | g/l |
| Part B Rochelle Salt in water | 50 | g/125 ml |
| Mix 1 l. H$_2$O + 75 ml A + 25 ml B | | |
| Silver Salt Solution B$_2$ | | |
| AgNO$_3$ | 100 | g/l |
| NH$_4$OH (conc.) | 10 | ml/l |
| Water | balance | |
| Silver Salt Solution B$_3$ | | |
| Ag F | 50 | g/l |
| NH$_4$OH (conc.) | 10 | ml/l |
| Water | balance | |
| Silver Salt Solution B$_4$ | | |
| Ag F | 100 | g/l |
| NH$_4$OH (conc.) | 10 | ml/l |
| Water | balance | |
| Silver Salt Solution B$_4$' | | |
| Ag F in water | 100 | g/l |
| Nickel Salt Solution C$_1$ | | |
| NiCl$_2$ . 6H$_2$O | 1.85 | g |
| NaOH | 4.55 | g |
| Rochelle Salt | 19.9 | g |
| Na$_2$CO$_3$ | 2 | g |
| H$_2$O | 125 | ml |
| Gold Solution D$_1$ | | |

-continued

| Copper Salt Solution A$_1$ | | |
|---|---|---|
| AuCl$_3$ | 0.25 | g |
| H$_2$O | 16.7 | ml |
| Na$_2$CO$_3$ | 1 | g |
| Formaldehyde | 0.65 | ml |
| Gold Solution D$_2$ | | |
| AuCl$_3$ | 0.25 | g |
| H$_2$O | 16.7 | ml |
| Na$_2$CO$_3$ | 1 | g |
| Reducing Solution R$_1$ | | |
| Formaldehyde in water | 37% | by weight |
| Reducing Solution R$_2$ | | |
| FeSO$_4$ in water | 25 | g/l |
| Reducing Solution R$_3$ | | |
| Hydrazine (N$_2$H$_4$) in water | 5 | ml/l |
| Reducing Solution R$_4$ | | |
| N$_2$H$_4$ in water | 1 | ml/l |
| Reducing Solution R$_5$ | | |
| N$_2$H$_4$ in water | 0.1 | ml/l |
| Reducing Solution R$_6$ | | |
| NaH$_2$PO$_2$ in water | 100 | g/l |
| Reducing Solution R$_7$ | | |
| SnF$_2$ in water | 100 | g/l |
| Reducing Solution R$_8$ | | |
| N$_2$H$_4$ in water | 2 | ml/l |
| Sensitizer Solution S$_1$ | | |
| SnCl$_2$ | 2.465 | g |
| Distilled water | 100 | ml |
| H$_2$O$_2$ | Several drops: sufficient to provide ≈0.01 M Sn$^{++++}$ | |
| HCl (37%) | 1.5 | ml |
| Activating Solution T$_1$ | | |
| Palladium chloride activator sold under the trade designation "Enplate Activator 440" by Enthonics Research | 30 | ml |
| Water | 450 | ml |
| Activating Solution T$_2$ | | |
| PdCl$_2$ | 0.093 | molar |
| HCl | 0.18 | molar |
| Water | balance | |
| Etching Solution X$_1$ | | |
| Acetic Acid (conc.) | 10% | (vol.) |
| Etching Solution X$_2$ | | |
| Hydrofluoric Acid (conc.) | 10% | (vol.) |
| Etching Solution X$_3$ | | |
| Phosphoric Acid (conc.) | 50% | (vol.) |
| Etching Solution X$_4$ | | |
| Hydrochloric Acid (conc.) | 10% | (vol.) |
| Etching Solution X$_5$ | | |
| Nitric Acid (conc.) | 10% | (vol.) |
| Etching Solution X$_6$ | | |
| Sulfuric Acid (conc.) | 10% | (vol.) |

EXAMPLE 2

A short length of vinyl tubing was fitted over the crown of an extracted human tooth and the surface of the tooth was activated by contacting it with activating solution T$_1$, at room temperature, introduced through the open end of the tube. After one minute, the activating solution was removed and sensitizing solution S$_1$, at room temperature, was introduced through the vinyl tube to contact the tooth. The sensitizing solution remained in contact with the tooth for a period of one minute, after which it was removed and the tooth was contacted for three minutes with copper salt solution A$_1$ at a temperature of 40° C. After removal of the warm copper solution, a room temperature plating solution consisting of 5 parts by weight copper solution A$_1$ and 1 part by weight reducing solution R$_1$ was placed in contact with the tooth for fifteen minutes. The plating solution and vinyl tube were then removed. A continuous copper plate was obtained on the areas of the tooth enclosed by the tube.

EXAMPLE 3

An extracted tooth was plated with copper in the manner described in Example 1, except that the activating, sensitizing and 40° C. salt solutions were applied directly to the tooth without introducing them through the vinyl tubing. The plating solution, however, was applied through the tubing. Again, a continuous copper plate was obtained on the crown of the tooth.

EXAMPLE 4

An extracted human tooth was plated in the manner described in Example 3, except that the sensitizing solution was only 0.001 molar with respect to stannic ions. A continuous copper plate was obtained over the crown of the tooth.

EXAMPLE 5

Utilizing the procedure described in Example 1, an extracted human tooth was treated in the following sequence:
 a. Activated for 1 minute with activating solution $T_1$ at room temperature
 b. Sensitized for 1 minute with sensitizing solution $S_1$ at room temperature
 c. Contacted with a 50 g./l. NaOH solution at 40° C. for 3 minutes
 d. Plated at room temperature with a solution consisting of 5 parts by weight of copper salt solution $A_1$ and 1 part by weight of reducing solution $R_1$
An excellent continuous plate was obtained.

EXAMPLE 6

An extracted human tooth was plated with copper in the manner described in Example 5, except that a room temperature sodium hydroxide solution was used in place of a 40° C. solution. A very good continuous copper plate was obtained.

EXAMPLE 7

An extracted human tooth was immersed in a 10% sodium hydroxide solution for 3 minutes and then sequentially immersed in activating solution $T_1$ for 1 minute and sensitizing solution $S_1$ for 1 minute. Following sensitization, the tooth was immersed for 15 minutes in a beaker containing silver salt solution $B_1$. A spotty silver deposit was obtained, indicating the desirability of including a reducing agent stronger than Rochelle salt in the aqueous plating mixture. Longer contact between the tooth and the plating mixture, however, would provide an adequate copper film where a relatively weak reducing agent such as Rochelle salt is utilized.

EXAMPLE 8

An extracted human tooth was etched with etching solution $X_1$ and then immersed sequentially in sensitizing solution $S_1$ and activating solution $T_2$, each for 1 minute. The activated tooth was immersed in silver salt solution $B_2$ for 1 minute, then in reducing solution $R_2$ for 1 minute, and again in silver salt solution $B_2$ for 1 minute. Next, the tooth was immersed for 15 seconds in copper salt solution $A_1$. A copper coating was obtained on the tooth.

EXAMPLE 9

An extracted human tooth was plated in the manner described in Example 8, except that a small portion of a copal-based dental varnish was applied to the surface prior to the commencement of plating operations. The entire tooth was plated with silver but the plating was easily removed in the area where the copal-based dental varnish was originally placed. Thus, copal-based dental varnishes may be effectively used as masking agents to allow selective plating of designated areas of the tooth.

EXAMPLE 10

An extracted human tooth was etched with etching solution $X_1$. In subsequently carrying out electroless plating, instead of immersing the tooth in the appropriate solutions, the solutions were applied by means of a cotton swab applicator ("Q-Tips" sold by Cheseborough-Ponds) which had been dipped in the appropriate solution. The saturated Q-tip was rubbed gently on the desired area of the tooth to apply the solutions used to effect plating. Each individual swabbing was carried out for approximately 5–10 seconds.

Following this procedure, the tooth was swabbed first with silver salt solution $B_2$ and then with reducing solution $R_2$. This sequence was repeated 6 times (6×). The tooth was then swabbed again with silver salt solution $B_2$ which followed swabbing by copper salt solution $A_1$. This sequence was also repeated 6 times (6×) producing a bright metallic silver deposit on the surface of the tooth.

EXAMPLE 11

A series of tests was carried out to provide a comparison of the effect of various etching solutions. Six different teeth were treated with various etching solutions and then each tooth was electrolessly plated by the same plating procedure. This procedure comprised swabbing the etched tooth alternately with silver salt solution $B_2$ and reducing solution $R_2$ (4×), and then alternately with silver salt solution $B_2$ followed by a plating mixture consisting of 4 parts copper solution $A_1$:1 part reducing solution $R_1$ (4×). The tooth was then given a final swab with silver salt solution $B_2$. Each tooth was successfully plated with silver in the area of the tooth which had been etched. The following visual observations were made on the teeth pretreated with the various etching solutions:

| Etching Solution | Time | Result |
| --- | --- | --- |
| $X_2$ | 1 min. | The unetched side was brighter than the etched side |
| $X_1$ | 1 min. | The unetched side received a spotty plate, while the etched side was continuous and bright |
| $X_3$ | 1 min. | Dark spots on the etched side but acceptable plating achieved |
| $X_4$ | 1 min. | Some darkening on the etched side |
| $X_5$ | 1 min. | Black spots on the etched side |
| $X_6$ | 1 min. | Some darkening on the etched side |

Dark spots indicate discontinuous areas. Further applications of plating mixtures are necessary to provide a continuous metal film over teeth on which dark spots are observed.

EXAMPLE 12

An extracted human tooth was plated by swabbing it in the following sequence (each swabbing operation being carried out for 5–10 seconds):
Silver solution $B_2$, then Reducing Solution $R_2$ (4×)
Silver solution $B_2$ (1×)
A plating solution was prepared by mixing nickel salt solution $C_1$ (5 ml), copper salt solution $A_2$ (5 ml), and water (30 ml). This mixed solution and copper salt solution $A_2$ were alternately swabbed onto the surface of the tooth (3×). A satisfactory plate was obtained and the continuity of the plating was checked by a conductivity test. The resistance of the plating so produced was measured using a Simpson Electric Company Model 263 volt-ohm milliameter and determined to be between about 1 and about 20 ohms/cm, indicating that a good film of metal was present.

EXAMPLE 13

An extracted human tooth was etched with etching solution $X_1$ and plated in the manner described in Example 11. After plating was completed, a small quantity of dental amalgam mix was placed on the tooth and carefully rubbed in. Additional amalgam was applied in small portions to avoid removal of the plated metal layer. A complete filling was gradually built up in this manner.

EXAMPLE 14

Three extracted human teeth were plated using the swabbing technique and hydrazine reducing solutions of varying concentrations.

A first tooth received alternate swabbing of silver salt solution $B_2$ followed by reducing solution $R_3$ (5 ml hydrazine/l) (4×). The rate of silver deposition was very rapid but an adherent silver plate was obtained.

A second tooth received alternate applications of silver salt solution $B_2$ followed by reducing solution $R_4$ (1 ml hydrazine/l) (4×). The plating rate was still quite rapid but not as fast as the rate experienced where reducing solution $R_3$ was used. A better overall silver film was obtained with reducing solution $R_4$ than with $R_3$.

A third tooth was plated in a manner similar to the first two, but reducing solution $R_5$ (0.1 ml hydrazine/l) was used. In this instance, the rate of silver deposition was slower than desired and the overall quality of the deposit not as good as the film obtained with higher concentrations of hydrazine.

EXAMPLE 15

An extracted human tooth was etched for 1 minute in etching solution $X_1$ and then alternately treated with silver salt solution $B_2$ and a second plating mixture comprising 4 parts copper salt solution $A_1$:1 part reducing solution $R_1$ (6×). The mixture of solutions $A_1$ and $R_1$ was preheated to 37° C. prior to application to the tooth. Application of the solutions was by swabbing. A good plate of silver was obtained with a very low resistance of 4 ohms/cm.

EXAMPLE 16

An extracted human tooth was etched with etching solution $X_1$ for 1 minute and then plated by sequential application of silver salt solution $B_2$, reducing solution $R_6$ and a third solution consisting of a mixture of 4 parts copper salt solution $A_1$:1 part reducing solution $R_1$ (3×). Application was by swabbing. A very shiny deposit having a 3,000 ohms/cm resistance was obtained.

EXAMPLE 17

An extracted tooth was plated in the manner described in Example 16, except that the plating sequence was carried out for 4× instead of 3×. A good deposit of silver was obtained, having a resistance of only 220 ohms/cm.

EXAMPLE 18

A series of plating runs was carried out on human extracted teeth using alternate applications of silver salt solution $B_2$ and a reducing solution of composition similar to $R_1$ except that the pH of $R_1$ was varied by inclusion therein of varying proportions of ammonium hydroxide. The teeth were plated by alternate swabbing with silver salt solution $B_2$ and reducing solution $R_1$ (4×). The resistance of the resultant metal films was measured and the films were observed visually as well. The results of these runs are set forth in the table below:

TABLE I

| pH | Resistance of Metal Deposit ohm/cm | Remarks |
| --- | --- | --- |
| 4 | 10,000 | Deposit shiny but appears thin |
| 7 | 4,000 | Good deposit |
| 8 | 3 | Very good deposit |
| 9 | 2,000,000 | Thin deposit |
| 10 | infinity | No deposit |

This data indicates that excessive proportions of ammonium hydroxide cause the silver ions to be strongly complexed and unavailable for deposition.

EXAMPLE 19

A series of runs identical to those described in Example 18 was carried out, except that the pH was adjusted using sodium hydroxide instead of ammonium hydroxide. The results of these runs indicate that the quality of the plate improved with increasing pH and no optimum was passed beyond which any detrimental effect was observed. The results of the runs of this example are set forth in the table below:

TABLE II

| pH | Resistance of Metal Deposit ohm/cm | Remarks |
| --- | --- | --- |
| 6.7 | 7×10$^5$ | Thin deposit |
| 8 | 400 | — |
| 9 | 375 | — |
| 11 | 30 | — |
| 12.5 | 15 | Good deposit |

EXAMPLE 20

An extracted human tooth was etched with etching solution $X_1$ and then alternately swabbed with silver salt solution $B_2$ and reducing solution $R_2$ (4×). Then the tooth was swabbed alternately with silver salt solution $B_2$ and a mixture of copper salt solution $A_1$ (4 parts) plus reducing solution $R_1$ (1 part) (4×). Next, the tooth was swabbed alternately with gold salt solution $D_2$ followed by a mixture constituted of copper salt solution $A_1$ (4 parts) plus reducing solution $R_1$ (1 part) (2×). The tooth plated well with a gold colored surface. X-ray analysis showed silver, gold and copper all to be present in the metal film.

EXAMPLE 21

An extracted human tooth was etched with etching solution $X_1$ and then swabbed alternately with gold salt solution $D_2$ and reducing solution $R_2$ (4×). Next, the tooth was swabbed alternately with gold salt solution $D_2$ and a mixture constituted of copper salt solution $A_1$ (4 parts) plus reducing solution $R_1$ (1 part) (6×). A good plate was obtained and X-ray analysis showed gold and copper to be present.

EXAMPLE 22

An extracted human tooth was etched with etching solution $X_1$ and then swabbed alternately with a mixture of copper salt solution $A_1$ (4 parts) and reducing solution $R_1$ (1 part) followed by gold salt solution $D_2$ (6×). A good plate was obtained exhibiting a resistance of 20 ohm/cm.

EXAMPLE 23

An extracted human tooth was swabbed alternately with silver salt solution $B_3$ and reducing solution $R_1$ (4×). Next, gold salt solution $D_1$ was swabbed on the tooth alternately with a mixture constituted of copper salt solution $A_1$ (4 parts) plus reducing solution $R_1$ (1 part) (4×). The tooth was then immersed in gold salt solution $D_1$ for 1 minute. A good plate was obtained having a resistance of 50 ohm/cm.

EXAMPLE 24

A series of extracted human teeth were swabbed alternately with silver nitrate solutions and reducing solution $R_2$ (4×). Each tooth was then alternately swabbed with silver nitrate solution and a mixture constituted of copper salt solution $A_1$ (4 parts) plus reducing solution $R_1$ (1 part) (4×). The concentration of the silver nitrate solution was constant throughout both plating operations on each tooth but the solution concentration was varied from tooth to tooth. The resistance of the film obtained on each tooth was measured and the following table indicates the resistance of the film as a function of the concentration of the silver nitrate solution:

TABLE III

| Concentration $AgNO_3$ (g/l) | Resistance of Metal Film (ohm/cm) |
|---|---|
| 20 | 27 |
| 7 | 65 |
| 5.5 | 120 |
| 3.5 | 400 |
| 2.5 | 1,000 |

EXAMPLE 25

Extracted human teeth were plated after etching for 1 minute in etching solution $X_1$. The teeth were swabbed alternately with silver salt solution $B_2$ and reducing solution $R_2$ (4×). Next, the teeth were swabbed alternately with silver salt solution $B_2$ followed by a mixture consisting of copper salt solution $A_1$ (4 parts) plus formaldehyde solution $R_1$ (1 part) (4×). The concentration of formaldehyde was varied and the resistance of the metal film obtained measured for each concentration of formaldehyde. The results of these runs are set forth in the table below:

TABLE IV

| Drops Formaldehyde per 20 ml $A_1$ | Resistance of Metal Film (ohm/cm) |
|---|---|
| 1 | 50,000 |
| 2 | 1,000 |

TABLE IV-continued

| Drops Formaldehyde per 20 ml $A_1$ | Resistance of Metal Film (ohm/cm) |
|---|---|
| 5 | 15 |

EXAMPLE 26

Extracted human teeth were brushed with sodium bicarbonate before plating. The teeth were then plated by swabbing alternately with silver salt solution $B_4$ and reducing solution $R_7$ (4×). Next, the teeth were swabbed alternately with silver salt solution $B_4$ and a mixture consisting of copper salt solution $A_1$ (4 parts) plus reducing solution $R_1$ (1 part) (2×). A good deposit was obtained exhibiting a resistance of 150 ohm/cm.

EXAMPLE 27

A tooth was plated in the manner described in Example 26, except that a wetting agent, benzalkonium chloride sold under the trade designation "Zephryn Chloride" by Winthrop Laboratories, was added to reducing solution $R_7$ (0.3 ml Zephryn Chloride/40 ml stannous fluoride solution). The appearance of the metal plating obtained was superior to that of Example 26, and the final resistance was measured at 90 ohm/cm.

EXAMPLE 28

Extracted human teeth were brushed and then etched with etching solution $X_1$. The teeth were then plated by swabbing alternately with silver salt solution $B_4$ and then with reducing solution $R_7$ (4×). Next, the tooth was subjected to alternate swabbing with silver salt solution $B_4$ followed by a mixture consisting of copper salt solution $A_1$ (4 parts) plus reducing solution $R_1$ (1 part) (4×). Good silver deposits were obtained on all teeth.

EXAMPLE 29

Extracted human teeth were swabbed alternately with silver salt solution $B_4$ and reducing solution $R_7$ (4×). The teeth were then swabbed alternately with silver salt solution $B_4$ and reducing solution $R_8$ (4×). A good silver deposit exhibiting a resistance of 100–300 ohm/cm was obtained.

EXAMPLE 30

Extracted human teeth were brushed and etched, and then plated by swabbing alternately with silver salt solution $B_4$ and reducing solution $R_7$ (2×). Next, the teeth were swabbed alternately with silver salt solution $B_4$ and reducing solution $R_8$. One tooth received the $B_4/R_8$ treatment for 1×, another for 2×, another for 4×, and another for 5×, giving respective resistances of infinity 85,000, 70 and 5 ohm/cm for the resulting plates.

EXAMPLE 31

Extracted human teeth were brushed and etched, and then swabbed alternately with silver salt solution $B_4$ and reducing solution $R_3$. One tooth was subjected to the $B_4/R_3$ treatment for 3×, another for 4×, and another for 5×, giving deposits with respective resistances of 3500, 60 and less than 1 ohm/cm.

In view of the above, it will be seen that the several objects of the invention are achieved and other advantages results attained.

As various changes could be made in the above methods without departing from the scope of the invention, it is intended that all matter contained in the above description shall be interpreted as illustrative and not in a limiting sense.

What is claimed is:

1. A dental procedure for providing a thin adherent substantially continuous metallic layer over a surface of a tooth comprising the steps of:
    contacting a surface of a tooth in a patient's mouth with an aqueous plating mixture containing a water-soluble salt of a metal selected from the group consisting of gold, silver, copper, nickel, platinum, palladium and tin and a reducing agent for the metal ions of said salt; and
    maintaining said mixture in contact with said surface for a time sufficient for an electrolessly deposited metallic layer to form thereon.

2. A dental procedure as set forth in claim 1 wherein said surface is repetitively contacted with said aqueous plating mixture to build up a continuous metal layer on said surface.

3. A dental procedure as set forth in claim 1 wherein said aqueous plating mixture is a solution at least about 0.25 molar with respect to the ions of said metal.

4. A dental procedure as set forth in claim 3 wherein said aqueous plating mixture further comprises a complexing agent for said metal ions.

5. A dental procedure as set forth in claim 1 wherein said aqueous plating mixture contains a proportion of said salt sufficient that said mixture contains on the order of 100 gpl of said metal.

6. A dental procedure as set forth in claim 1 wherein said aqueous plating mixture is maintained at a temperature between about room temperature and about 45° C. when said surface is contacted therewith.

7. A dental procedure as set forth in claim 6 wherein said aqueous plating mixture is maintained in contact with said surface for a period of between about 2½ and about 5 minutes.

8. A dental procedure as set forth in claim 1 wherein said metal is silver.

9. A dental procedure as set forth in claim 1 wherein said reducing agent is selected from the group consisting of formaldehyde, hydrazine, dimethylaminoborane, alkali metal formates, and alkali metal hypophosphites.

10. A dental procedure as set forth in claim 9 wherein said reducing agent is formaldehyde and said plating mixture is maintained at a pH of at least about 8.5.

11. A dental procedure as set forth in claim 10 wherein said aqueous plating mixture contains a silver salt and ammonium hydroxide and the pH of said mixture is maintained below about 10.

12. A dental procedure as set forth in claim 1 wherein said aqueous plating mixture is a slurry whose solid phase comprises said salt.

13. A dental procedure as set forth in claim 1 wherein a discontinuous layer of an activating metal is initially deposited in said surface, thereby providing nuclei for the subsequent deposition of said metallic layer.

14. A dental procedure as set forth in claim 13 wherein said activating metal is palladium and said surface is activated by the steps of:
    contacting said surface with an activating solution containing palladium ions; and
    contacting said surface with a sensitizing solution containing stannous ions.

15. A dental procedure as set forth in claim 13 wherein said activating metal is silver, said surface is activated by its initial contact with an aqueous plating mixture containing a silver salt, and a continuous silver layer is subsequently deposited by repeated contact of said surface with said plating mixture.

16. A dental procedure as set forth in claim 1 further comprising contacting said metallic layer with an aqueous cementation solution containing ions of a second metal having a lower oxidation potential than the metal of said layer, thereby causing oxidation of the metal of higher oxidation potential and displacement thereof from the surface of said layer with concomitant reduction of the ions of said second metal to the elemental state and deposition of said second metal on the surface of said layer.

17. A dental procedure as set forth in claim 16 wherein the surface of the tooth is alternately and repetitively contacted with said aqueous plating mixture and said cementation solution.

18. A dental procedure as set forth in claim 17 wherein said plating mixture comprises a copper salt and said cementation solution comprises a silver salt.

19. A dental procedure as set forth in claim 1 wherein said layer has a thickness on the order of about 1 to about 10$\mu$.

20. A dental procedure as set forth in claim 1 wherein the resistance across said layer is between about 1 and about 10 ohms/cm.

21. A dental procedure as set forth in claim 1 wherein said surface is chemically etched prior to being contacted with said aqueous mixture.

22. A dental procedure as set forth in claim 1 wherein said aqueous plating mixture further comprises a wetting agent.

23. A dental procedure as set forth in claim 1, further comprising:
    electrically connecting the negative terminal of a direct current power source to said metallic layer;
    providing an electrolytic metal plating solution in contact with said layer and with an anode electrically connected to the positive terminal of said power source; and
    applying a direct current to cause electrolytic deposition of metal from said plating solution on said metallic layer.

24. A dental procedure for sealing a surface of a tooth comprising the steps of:
    contacting a surface of a tooth in a patient's mouth with an aqueous plating mixture containing a water-soluble salt of a metal selected from the group consisting of gold, silver, copper, nickel, platinum, palladium and tin and a reducing agent for the metal ions of said salt;
    maintaining said mixture in contact with said surface for a time sufficient for the metal ions of said salt to be reduced and form an electrolessly deposited metallic sealing layer on said surface; and
    applying over said metallic sealing layer a further sealing material which adheres to said metallic layer.

25. A dental procedure as set forth in claim 24 wherein said further sealing material comprises a material capable of alloying with said metallic layer.

26. A dental procedure as set forth in claim 25 wherein said further sealing material comprises a dental amalgam.

27. A dental restorative procedure for adherently applying a restorative material in an excavation made in the course of a tooth restoration comprising the steps of:

contacting a surface of a tooth excavation in a patient's mouth with an aqueous plating mixture containing a water-soluble salt of a metal selected from the group consisting of gold, silver, copper, nickel, platinum, palladium and tin and a reducing agent for the metal ions of said salt;

maintaining said mixture in contact with said surface for a time sufficient for the metal ions of said salt to be reduced and form an electrolessly deposited metallic layer on said surface; and applying a tooth restorative material over said metallic layer.

28. A procedure as set forth in claim 27 wherein said tooth restorative material is a dental amalgam.

* * * * *